United States Patent
Bergaud et al.

(10) Patent No.: US 6,930,365 B2
(45) Date of Patent: Aug. 16, 2005

(54) BIOSENSOR MATRIX AND METHOD FOR MAKING SAME

(75) Inventors: Christian Bergaud, Toulouse (FR); Benoît Belier, Orsay (FR); Augustin Martinez, Orens (FR); Nicu Livus, Aragon (FR); Emeline Cocheteau, Toulouse (FR)

(73) Assignee: Centre National de la Recherche, Paris (FR)

( * ) Notice: Subject to any disclaimer, the term of this patent is extended or adjusted under 35 U.S.C. 154(b) by 26 days.

(21) Appl. No.: 10/475,324

(22) PCT Filed: Apr. 25, 2002

(86) PCT No.: PCT/FR02/01419

§ 371 (c)(1),
(2), (4) Date: May 4, 2004

(87) PCT Pub. No.: WO02/086479

PCT Pub. Date: Oct. 31, 2002

(65) Prior Publication Data

US 2004/0185592 A1 Sep. 23, 2004

(30) Foreign Application Priority Data

Apr. 25, 2001 (FR) .............................. 01 05545

(51) Int. Cl.[7] .......................... H01L 27/14; H01L 29/82
(52) U.S. Cl. ......................................... 257/414; 438/48
(58) Field of Search ................................ 257/414, 415, 257/420, 417, 466; 438/48, 50, 52

(56) References Cited

U.S. PATENT DOCUMENTS

| 5,184,515 | A | * | 2/1993 | Terry et al. ................... 73/727 |
| 5,252,294 | A | | 10/1993 | Kroy et al. |
| 5,631,198 | A | | 5/1997 | Hartauer |
| 5,719,324 | A | | 2/1998 | Thundat |
| 6,054,277 | A | | 4/2000 | Furcht |
| 6,329,139 | B1 | * | 12/2001 | Nova et al. ..................... 435/6 |
| 6,743,654 | B2 | * | 6/2004 | Coffa et al. ................... 438/52 |
| 2004/0152228 | A1 | * | 8/2004 | Benzel et al. ................. 438/50 |

FOREIGN PATENT DOCUMENTS

| WO | WO 95/01559 | 1/1995 |
| WO | WO 00/66266 | 11/2000 |

OTHER PUBLICATIONS

XP–002189581—"Ultra–shallow raised p<+>n junctions with self–aligned titanium silicide contacts formedby boron outdiffusion from selectively deposited silicon epitaxial layers" c. 1995.

"Rapid thermal processing of piezoresistive polycrystalline silicon films: an innovative technology for low cost pressure sensor fabrication" c. 1995.

* cited by examiner

Primary Examiner—W. David Coleman
(74) Attorney, Agent, or Firm—Clark & Brody

(57) ABSTRACT

The invention relates to a biosensor matrix comprising a substrate made of semiconductor material. It has a main plane surface and cavities formed in a surface opposite from said plane surface to define between the bottoms of said cavities and the main plane surface deformable structure each including at least one piezoresistive or piezoelectric sensing element. The method of manufacture implements fabrication techniques specific to micro- and nanotechnologies, preferably with localized pre-amorphization of the surface of the substrate prior to implantation of piezoelectric elements, which implantation is followed by annealing.

19 Claims, 4 Drawing Sheets

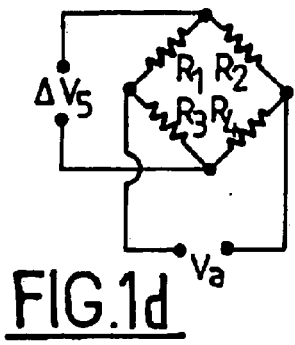
FIG.1d
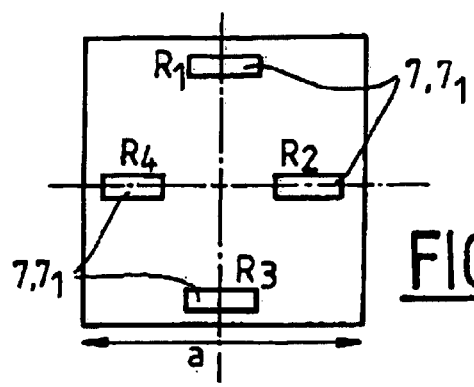
FIG.1c
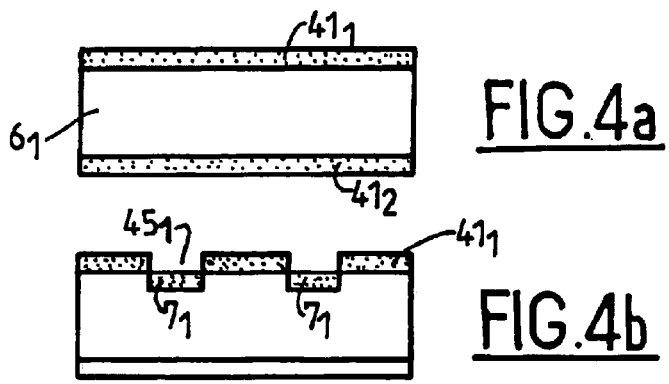
FIG.4a
FIG.4b
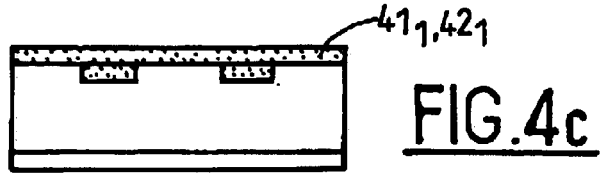
FIG.4c
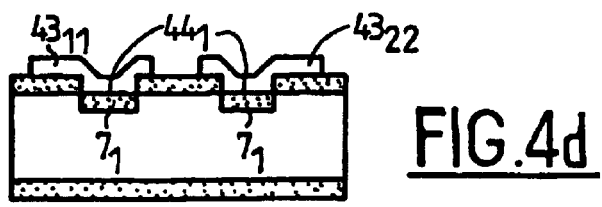
FIG.4d
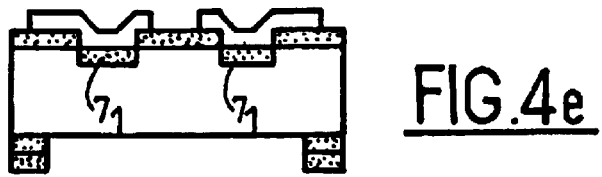
FIG.4e
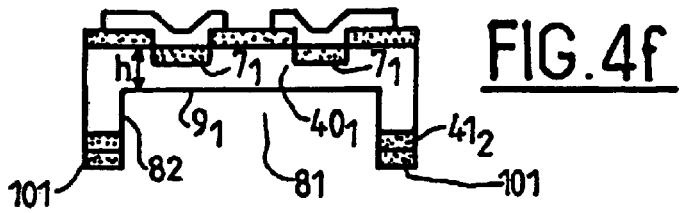
FIG.4f

BIOSENSOR MATRIX AND METHOD FOR MAKING SAME

The present invention relates to a matrix of biosensors using the piezoresistive effect or the piezo-electric effect to detect specific molecular interactions. The invention also relates to a method of fabricating the matrix.

BACKGROUND OF THE INVENTION

Proposals have already been made, for example in U.S. Pat. Nos. 5,719,324 and 6,054,277 to implement a biosensor integrated on a semiconductor chip, the biosensor having one or more levers, each fixed at one end.

Technical progress requires a large number of measurements to be made and consequently to have a larger number of biosensors. Unfortunately, prior art techniques allow only individual biosensors to be made, which leads to large fabrication costs that it is highly desirable to reduce.

OBJECTS AND SUMMARY OF THE INVENTION

For this purpose, the method proposes a technique for enabling a large number of biosensors to be integrated on a common semiconductor substrate.

The invention thus provides a matrix of biosensors comprising a substrate of semiconductor material, the matrix presenting a "main" plane surface, and cavities formed in a plane surface opposite from said main surface. Deformable structures, each comprising at least one piezoresistive or piezoelectric sensing element, are disposed between the bottoms of said cavities and the main plane surface.

The cavities are thus open cavities opening out in the surface opposite from the main plane surface.

In a preferred embodiment, at least one deformable structure is a membrane.

Alternatively, a deformable structure may comprise at least one beam fixed at one or preferably at both ends, e.g. by implementing localized surface attack.

Advantageously, at least one deformable structure presents a plurality of said sensing elements connected in a bridge circuit.

The substrate may be made of silicon, and may preferably be of a type presenting a buried layer of $SiO_2$ (a silicon on insulator (SOI) substrate).

In a first variant, at least one deformable structure integrates at least one piezoresistive sensing element.

In a second variant, at least one deformable structure presents at least one piezoelectric sensing element disposed on the substrate.

For electrical connection purposes, in particular for multiplexing the sensing elements, the plane surface advantageously presents metallization.

The invention also provides a method of fabricating a biosensor matrix of the above-specific type, the method implementing:

a) making said sensing elements in first localized locations of the main plane surface of the substrate; and b) making said cavities at second localized locations in a second surface of the substrate which is opposite from the main plane surface, in order to obtain deformable structures, each including at least one said sensing element.

In the method, said sensing elements are piezoresistive, the substrate is made of silicon, optionally including a buried layer of silica ($SiO_2$) surmounted by a single-crystal surface layer, step a) comprises:

$a_1$) depositing a masking layer on a first surface of the substrate, e.g. on the single-crystal surface layer;

$a_2$) making openings at first localized locations in the masking layer; and $a_3$) implanting ions in order to make said piezoresistive sensing elements;

and step b) comprises:

$b_1$) depositing a masking layer on a second surface of the substrate opposite from said first surface;

$b_2$) making openings in second localized locations of the masking layer; and $b_3$) making said cavities by chemical attack. For a substrate provided with a buried layer of $SiO_2$, the attack may be continued as far as the $SiO_2$ layer, which forms a stop layer, said layer of $SiO_2$ either being retained or else subsequently being removed in part, e.g. to form a passivation layer.

Alternatively, the $SiO_2$ layer may be removed entirely.

Advantageously, step $a_3$) implements:

$a_{31}$) implanting ions containing boron, e.g. boron fluoride; and $a_{32}$) thermal annealing.

Step $a_{31}$ is preferably preceded by pre-amorphization of the surface of the substrate at said first localized locations of the masking layer, e.g. by implanting germanium.

Advantageously, the method implements making electrical contact electrodes for the piezoresistive sensing elements.

In another variant, the sensing elements are piezoelectric, and step a) includes depositing a piezoelectric layer on said first localized locations, followed by crystallization annealing.

The method advantageously implements electrical contact electrodes for the piezoelectric sensing elements.

BRIEF DESCRIPTION OF THE DRAWINGS

Other characteristics and advantages of the invention appear better on reading the following description given by way of non-limiting example, with reference to the drawings, in which:

FIGS. 1a and 1b show an embodiment of a matrix of the invention, FIG. 1b being an enlargement of a detail of FIG. 1a; FIG. 1c shows a preferred embodiment, and FIG. 1d shows a Wheatstone bridge circuit;

FIGS. 4a to 4f show another method of fabrication starting from an Si substrate, in particular a single-crystal substrate.

MORE DETAILED DESCRIPTION

Figure 1A:
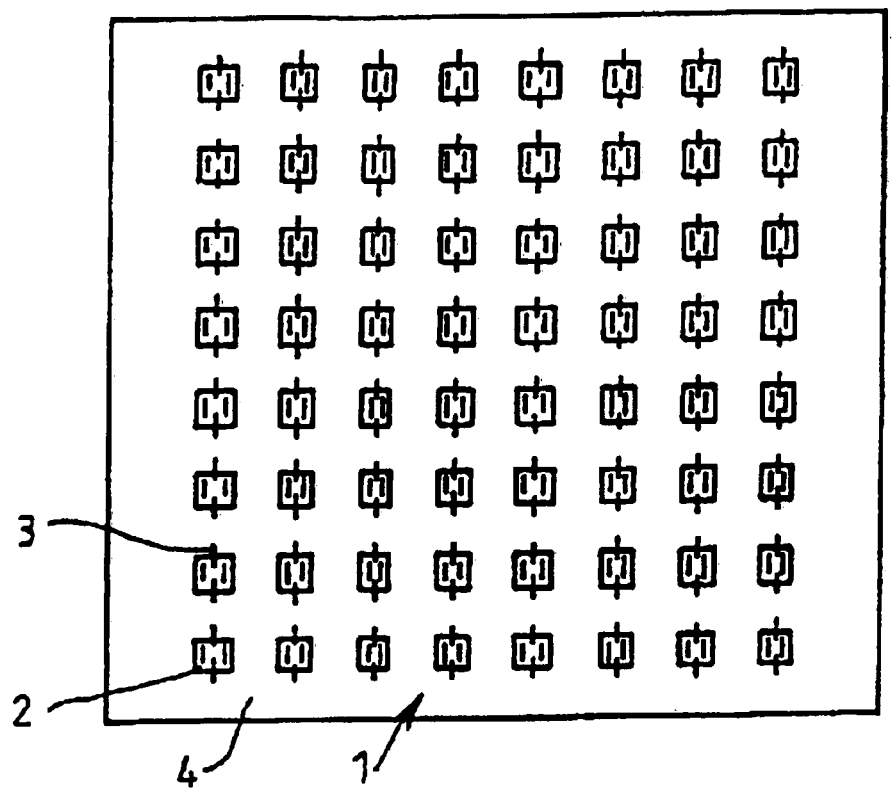

The invention relates to the field of genomics, proteomics (DNA chips, protein chips), and more generally biochips. It relates to a device for detecting specific interactions, of oligonucleotides (DNA/DNA; DNA/RNA) or of proteins (DNA/proteins) or of antigens-antibodies.

Such a system makes it possible to avoid the use of probe marking techniques and thus of external detection systems using fluorescence or radioactivity.

The proposed principle for detection can be compared with that of quartz crystal microbalances in which a change in mass leads to a change in resonant frequency and/or of the damping of a structure at resonance.

Nevertheless, in the context of the invention, the use of thin sensing elements of the piezoelectric or preferably of the piezoresistive type makes it possible to improve performance particularly in terms of sensitivity compared with quartz crystal microbalances in which the Q factor must be very high in order to achieve sensitivity that is sufficient.

In the context of the invention, the variations in mass that are to be detected are due to the pairing of target DNA (or RNA, or proteins, or any type of inter-molecule interaction) with DNA probes present on the sensing element.

The technique of the invention makes it possible on a single substrate to implement a multitude of independent resonant structures of small dimensions, e.g. a few microns, instead of a single device only as is the case in the prior art. This approach is possible because the techniques of preparing ultrathin piezoresistances or ultrathin piezoelectric layers are compatible with silicon technologies, thus making it possible to fabricate resonant microstructures simultaneously and at low cost.

Furthermore, reducing the dimensions of these microstructures serves to reduce their mass. Thus, the smaller the mass of the resonant structures, the greater the change in the response of said structure in response to the addition of a given mass, so the sensitivity of the system is thus increased.

In the context of the present invention, it is preferable to use piezoresistive sensing elements, and in particular membranes. This presents two advantages:

1/ In static mode, while preparing the DNA chip and during which the biological material is deposited by contact on the piezoresistive microdevices by an automated deposition system, the deformable membranes enable the bearing force and the duration during which said force is applied to be controlled very precisely, thus ensuring quality control over the solution deposited on the microdevice. This type of control is not possible with structures of the type comprising a beam fixed at one end as are used in some cases for detecting interactions, for example a beam as described in U.S. Pat. No. 5,807,758.

In addition, with the proposed system, if contact deposition systems are used, then during the static stage, during deposition it is possible to determine the force and the length of time the needles press against the devices where deposits are being made. If a contactless deposition system is used (a microfluidic system with droplets being ejected), then the system of the invention makes it possible to determine the quantity of liquid that is deposited, the mass of the droplets leading to a change in stress and thus to a change in piezoresistance (or a piezoelectric effect).

This is an important point since it is thus possible to identify faulty alignment between the various needles used for performing simultaneous depositions, possible needle wear, or indeed differences concerning the contact times of different points, or even differences concerning the sizes of droplets, as exist very often in droplet ejection systems.

The ability to perform such detection is important since it determines deposition quality (volume and thus concentration deposited, and reliability of results).

The system is compatible with active control of deposition using a feedback loop enabling errors to be corrected as a function of contact force and time during deposition.

Alternatively, the method may be used to calibrate contact deposition systems by adjusting the heights of the points, to verify wear and the effects of mechanical drift in the system, or indeed the effects of parasitic interactions such as vibration, or even to calibrate contactless deposition systems to adjust the droplet ejection frequency or indeed the distance between the ejection zone and the surface of the microdevice.

Such a calibration device can be used before or after making a series of deposits with a contact system, and after making a deposit with a contactless system.

2/ In dynamic mode, during the detection stage, the membranes serve to provide effective mechanical decoupling between the various resonating micro devices.

This makes it possible to avoid possible parasitic interactions via the substrate between the various modes of resonance of each microdevice. Such a phenomenon is likely to arise if the microdevices are deposited directly on the initial substrate.

This dynamic mode may also be used for the deposition stage in the same manner as that described above under point 1/ for controlling the quality of deposition.

The fabrication method is described below.

From a technological point of view, the requirement is to fabricate membranes (or beams) of dimensions that are as small as possible, which assumes that the thickness of the piezoresistances is reduced accordingly. For this purpose, the invention makes use of localized pre-amorphization of the substrate followed by implanting boron or boron fluoride, in particular at very low energy, e.g. 15 kiloelecton volts (keV), associated with fast thermal annealing. For example annealing for a period of 1 second (s) to 10 s at a temperature in the range 900° C. to 1100° C. enables the looked-for results to be obtained.

Ultrathin $p^+/n$ junctions are thus obtained which present piezoresistive characteristics.

In the context of the intended application, the membranes (which are advantageously square or rectangular in shape, and optionally circular) are made of single-crystal silicon, for example, being of uniform thickness (a few microns to a few hundreds of microns), of (100) orientation, and having edges parallel to the <110> directions. By way of example, the substrate is of n type doped at $10^{17}$ atoms per cubic centimeter (atoms/cm$^3$). Piezoresistances (or piezoresistive strain gauges having a nominal resistance of about 1 kiloohm (kΩ) to 10 kΩ (typically a few kΩ, for example in the range 4 kΩ to 4.5 kΩ) are implanted so as to confer them with doping, in particular P$^+$ doping, lying in the range $10^{18}$ to $10^{19}$ atoms/cm$^3$. The length of these strain gauges lies in the range 50 microns ($\mu$m) to a few hundreds of microns (e.g. 50 $\mu$m to 500 $\mu$m) and their width lies in the range 10 $\mu$m to a few tens of $\mu$m (e.g. 10 $\mu$m to 50 $\mu$m or 100 $\mu$m). The thickness h of the membrane is selected, for example, to lie in the range 2 $\mu$m to 30 $\mu$m, for example it is made to be equal to 15 $\mu$m. The membrane can be square, for example, having a side a=500 $\mu$m. A Wheatstone bridge circuit serves to compensate for thermal drift of the resistance value by rejecting common mode. A reduction in the size of the strain gauges makes it possible to optimize the mean stress seen by each gauge, and thus to optimize sensitivity. This reduction must be compatible with the tolerances of the fabrication method used, in order to avoid excessively increasing the dispersion in the resistances of the strain gauges.

The applied force F can be approximated by the following formula (R=R1=R2=R3=R4).

For a square membrane of single-crystal Si having a side a and a height h:

$$F = \frac{2\Delta Vs}{Va} \frac{h^2}{\pi_{44} 6 \times 0.1257\left(\frac{1}{v} - 1\right)}$$

$v=0.26$ (Poisson coefficient) giving for $h=15$ $\mu$m, $a=500$ $\mu$m, and $Va=10$ volts (V):

F1=4.05 micronewtons (mN) for $\Delta Vs_1$=0.534 V

F2=2.60 mN for $\Delta Vs_2$=0.343 V and for a circular membrane of single-crystal silicon of height h:

$$F = \frac{4}{3} \frac{\Delta Vs}{Va} \frac{\pi}{\pi_{44}} \frac{h^2}{(1-v)}$$

with $\pi_{44}$=138.1 $e^{-11}$ (in reciprocal Pascals (Pa$^{-1}$))

$v=0.26$

Va=the voltage applied to the Wheatstone bridge $\Delta Vs$=the voltage difference across the terminals of the Wheatstone bridge (see FIG. 1d).

Specifically: $h=15$ $\mu$m, $a=500$ $\mu$m, and Va=10 V, giving:

F1=32.07 nM for $\Delta Vs_1$=0.467 V, and

F2=12.43 mN for $\Delta Vs_2$=0.181 V

In practice, the sensor can be calibrated by measuring voltage variations picked up across the terminals of the Wheatstone bridge when calibrated forces are applied to the membrane.

The technique described presents the advantage of leading to beam-shaped piezoresistive sensors that present sensitivity that is very greatly improved compared with the sensitivity obtained by conventional techniques of implanting boron which leads to junction depth values that are greater. This improvement comes from the fact that the combination of the two techniques described above (pre-amorphization and implantation) associated with rapid thermal annealing techniques makes it possible to confine the piezoresistive zone accurately to the surface of the device where mechanical stress is at a maximum during deflection, whether in static mode or in dynamic mode.

The advantage of the technique of the invention is that it provides piezoresistances having very shallow junction depth, in particular in the range 50 nanometers (nm) to 200 nm, or indeed in the range 50 nm to 100 nm, for example being equal to 70 nm, with a conventional starting substrate of Si, e.g. doped at $10^{17}$ atoms/cm$^3$, in which the boron is implanted at an energy of 15 keV. In comparison, implanting boron followed by conventional annealing can lead to junction depths lying in the range 0.3 $\mu$m to 0.4 $\mu$m.

This technique of preparing an ultrathin piezo-resistance combining pre-amorphization, boron or BF$_2$ implantation at low energy, associated with fast thermal annealing can be used equally well to fabricate membranes that include piezoresistive sensors or that include piezoresistive levers in the context of the present invention (also entirely suitable for atomic force microscopy).

Nevertheless, it should be observed that it is much more advantageous in the context of the intended application to obtain a membrane that is continuous, which means that the main face of the substrate remains leakproof and that it can be used like a conventional glass slide without any need to proceed with special cleaning operations between two successive uses of the biochip.

The invention is described below for obtaining a matrix of biosensors comprising membranes having a thickness of 5 microns, for example, each integrating four piezoresistances in a Wheatstone bridge circuit. A gold area can be deposited on each device, e.g. an area having a diameter of 200 $\mu$m and suitably insulated from electrical contact points, thus making it possible to locate molecular interactions (chemical interaction on gold with grafting chemistry specific for gold).

The unloaded mechanical resonances (fundamental mode) of the microdevices can be measured electrically via variations in the piezoresistances. A calibration protocol serves to measure variation in resonant frequency following pairing of complementary strands of DNA, following an antigen-antibody interaction, a DNA/proteins interaction, etc . . . .

Figure 1B:
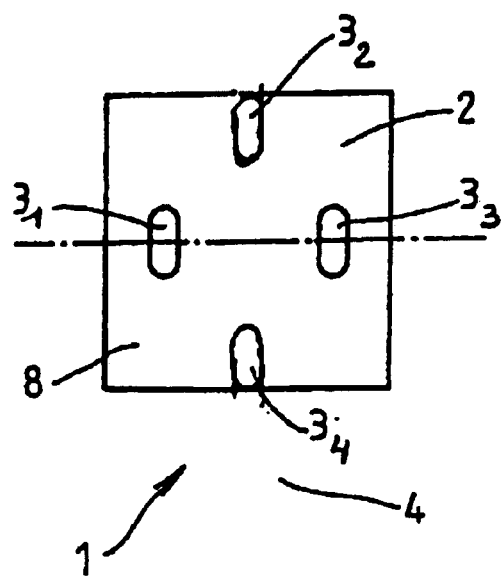

A matrix of biosensors of the invention is shown in FIG. 1a. It presents a two-dimensional array of biosensors, each comprising a membrane 2 and a plurality of piezoresistive or piezoelectric sensing elements. As shown more particularly in FIG. 1b, the sensing elements referenced $3_1$, $3_2$, $3_3$, and $3_4$ are placed in such a manner as to enable detection to be performed when they are selected as a Wheatstone bridge. Each of the membranes 2 is defined between a plane main face referenced 4 of the substrate 1 and the bottom 9 of the cavity that is open in its top portion (in its configuration of use which is upside-down relative to that which is shown in order to illustrate the method of fabrication), which cavity is made in the substrate (see FIG. 2e). In the preferred embodiment which is shown in FIG. 1c, the strain gauges all have the same resistance R1 to R4, and they are situated in the middle of each edge of a square (or rectangular) membrane of side a, such that the strain gauges lie in zones of maximum stress and the responses of the strain gauges have identical absolute values. Variations in the resistances R2 and R4 are opposite in sign to variations in the resistances R1 and R3, which is why they are connected in a Wheatstone bridge circuit as shown in FIG. 1d. This configuration minimizes the thermodynamic stresses generated by the interconnections for the membrane.

A fabrication method for making piezoresistive sensing elements is described below with reference to FIGS. 2a to 2f, starting from a substrate 1 which presents a buried layer 5 of SiO$_2$ surmounted by a surface layer 6 having a thickness of a few microns (for an SOI type substrate), which thickness can be less than 1 micron for a SIMOX type substrate.

Figure 2A:
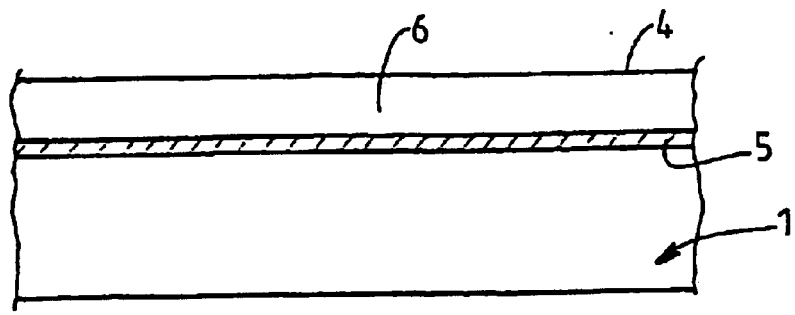
FIGS. 2a to 2e show the method of fabricating a matrix presenting piezoresistive elements.
Figure 2B:
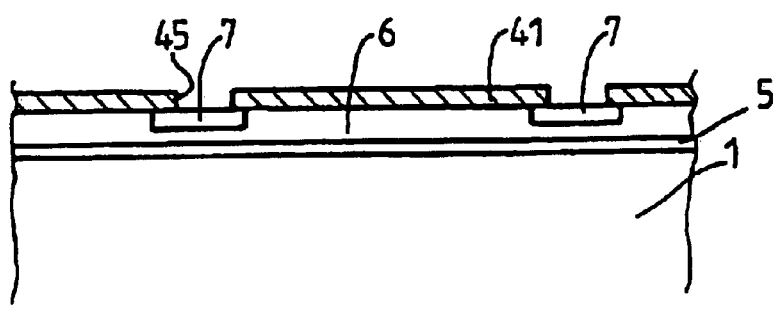
Figure 2C:
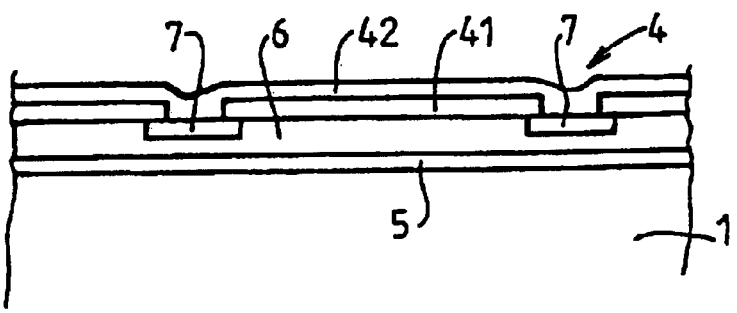

In FIG. 2b, an oxide layer 41 has been deposited on the surface of the substrate, and openings 45 are made therein to enable the piezoresistances to be made. An optional first implanting step is performed in which germanium is implanted to pre-amorphize the surface layer 6 locally. Thereafter, boron B or boron fluoride BF$_2$ is implanted at a density of $10^{14}$ atoms/cm$^2$ (e.g. to make the zones 7 constituting the piezoresistances). Thereafter, rapid thermal annealing (RTA) is performed (e.g. using a halogen lamp) for a duration of a few seconds to a few tens of seconds and at a temperature in the range 900° C. to 1100° C., said rapid treatment optionally being followed by conventional annealing at lower temperature, e.g. for 20 minutes at 800° C., with the combination of these treatments making it possible to activate the implanted atoms of boron (or of BF$_2$) electrically, and to reduce the defects created during ion implantation.

Figure 2D:
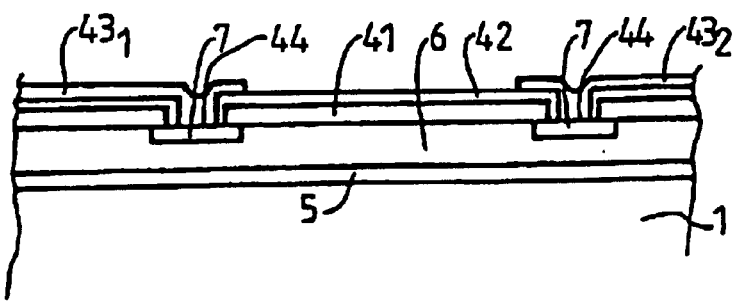

Thereafter the substrate is passivated (FIG. 2c) by depositing an oxide layer 42, e.g. by cold chemical vapor deposition (CVD) under a plasma, e.g. plasma-enhanced CVD (PECVD) or low-pressure CVD (LPCVD). Metallization with aluminum is then performed to make electrical conductors $43_1$ and $43_2$ to make contacts 44 on the piezoresistive sensing elements 7 (FIG. 2d).

Figure 2E:
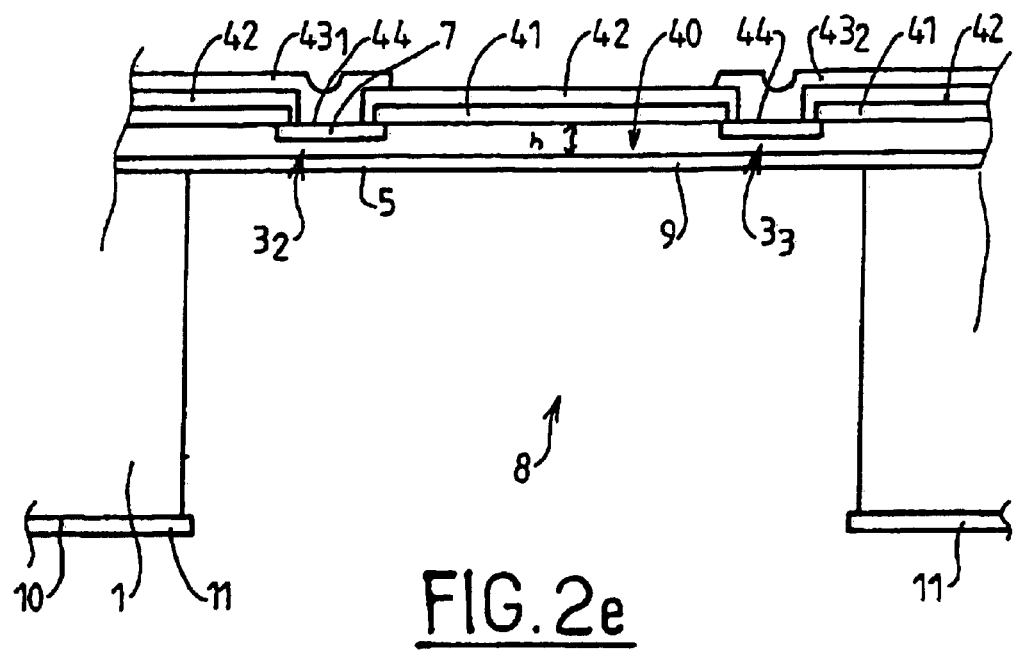

Thereafter, as shown in FIG. 2e, open cavities 8 are made from the rear face 10 of the substrate 1 by deep dry ionic etching after masking with a thick layer of resin 11.

It is also possible to implement wet etching of the tetramethyl ammonium hydroxide (TMAH) or potassium hydroxide (KOH), or ethylene diamine pyrocatechol (EDP), but in this case a layer of nitride 11 is used as the masking layer.

In either case, the interfacial layer 5 of silicon oxide in the substrate 1 serves as a stop layer for the etching.

This layer 5 is subsequently optionally removed by dry reactive ion etching (RIE) from the rear face, which is recommended rather than using a chemical solution of hydrofluoric acid, since that can damage the front face of the device.

Each open cavity or well 8 then presents a thin membrane 40 having piezoresistances $3_1$ to $3_4$ or R1 to R4 integrated therein (corresponding to the zones 44).

A variant of the method is shown in FIGS. 4a to 4f. The starting material is a silicon substrate Si which has been subjected to oxidation on both faces (dual oxidation $41_1$, $41_2$, FIG. 4a). Thereafter, optionally after pre-amorphization, B or $BF_2$ is implanted through openings $45_1$ to make the piezoresistances $7_1$ (FIG. 4b) This implantation is followed by implantation annealing and by thermal oxidation to isolate the piezoresistances (oxidation $41_1$, $42_1$, FIG. 4c). Thereafter, openings are made in the oxide layer $41_1$, $42_1$ to make contacts $44_1$ by aluminum metallization, and then the contacts are etched and the aluminum is annealed so as to obtain metallizations ($43_{11}$, $43_{22}$ FIG. 4d). A resin layer $10_1$ is deposited which is exposed so as subsequently to open the oxide $41_2$ on the rear face (FIG. 4e). Thereafter, deep dry etching is performed from the rear face in order to form the open cavities 81 and the membranes $40_1$ (FIG. 4f). Each of the (square or rectangular) cavities 81 is defined by a bottom 91 and by four side walls 82. In general, the steps of this method are implemented in the same way as for the method of FIGS. 2a to 2e except that the substrate is made of Si without a buried oxide layer.

The proposed configuration can be adapted to any robotic system for depositing samples that enables droplets to be deposited of volume that does not exceed a few nanoliters. By way of example, contact deposition systems using microneedles or using piezoelectric systems are suitable.

The matrix of biosensors makes it possible to devise an integrated detection system relying on fine measurements of variation in mass following hybridization or an interaction between biological molecules by using a piezoresistive or a piezoelectric system deposited on a membrane (or on a beam).

From a qualitative point of view, this device makes it possible to detect interactions between biological molecules, and from a quantitative point of view it enables the quantity of molecules that have interacted to be measured, and it also makes it possible to follow the reaction kinetics, without it being necessary to have recourse to steps of marking biological molecules with radioactive or fluorescent markers.

The use of micro- and nanotechnology enables the biosensor matrix to be mass-produced at low cost. Given that measurement is based on the principle of measuring variation in mass, the molecules do not require prior marking. The use of such sensors enables detection to be performed quickly and in quantitative manner, and also makes it possible to track the kinetics of the intermolecular reaction in real time.

Reducing the size of the resonant devices as is made possible by the technique used, makes it possible to obtain resonant frequencies that are high, typically several megahertz (MHz), with a high Q factor leading to an increase in sensitivity. In addition, the low mass of the active part of the microdevices makes them correspondingly more sensitive to the slightest variation in mass due to pairing with a complementary species.

Measurements can be performed in a vacuum, in which case it is necessary to make use of washing and drying steps after hybridization. Measurements can also be performed in a liquid medium, in which case the drying step is not performed.

In a vacuum, it is preferable to measure variation in resonance or in impedance, while in a liquid it is preferable to measure viscous damping.

Because the biosensor array comprises a large number of resonant structures, it is possible to perform statistic analysis of the data if the same deposition is performed on each of the structures, or else to work simultaneously using a plurality of types of deposition.

The main advantages of the biosensor matrix of the invention are thus:

1) low fabrication costs by using a simultaneous fabrication technique (micro- and nanotechnologies);

2) it is possible to fabricate the resonant structures of very small dimensions simultaneously in an array, thereby increasing sensitivity and integration density;

3) it is possible to work on small working volumes, thus reducing the time needed for analysis and also the cost of fabricating the chip;

4) it is possible to track in situ the kinetics of the reactions involved;

5) it is possible to detect hybridization reactions without having recourse to fluorescence or radioactivity type marking techniques;

6) it is possible to reuse structures merely by washing them or by heating them to a temperature compatible with dehybridization (in the range 50° C. to 60° C.); and 7) reading can be automated and the results can be given very quickly.

Figure 3:
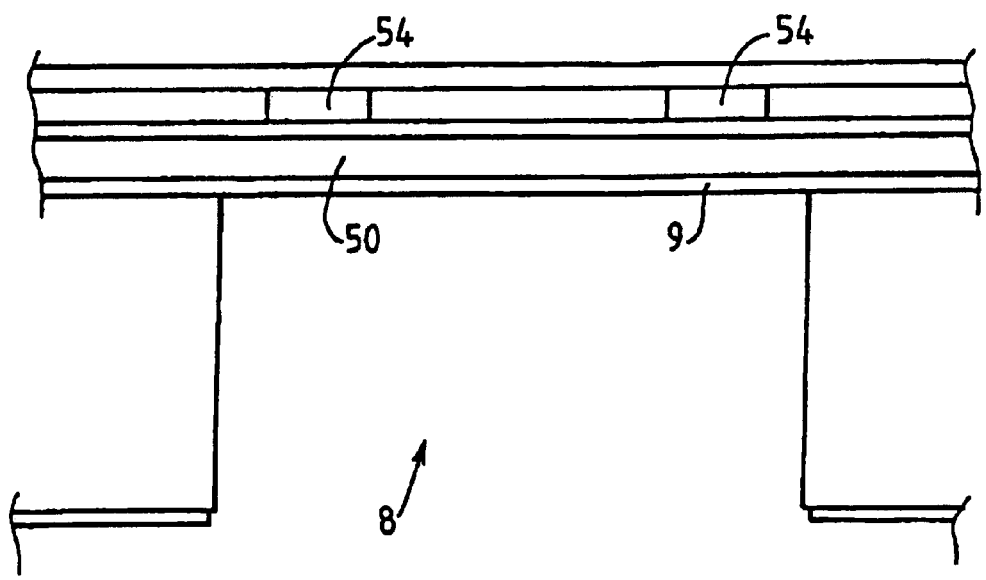
FIG. 3 shows a method of making the invention in which the sensing elements are piezoelectric.

The invention can also be performed by performing a conventional method to make piezoelectric sensing elements 54 deposited at localized locations on the main surface of the substrate (see FIG. 3). Open cavities 8 are then formed as described above so as to constitute deformable structures 40 (membrane or beam fixed at one or both ends).

What is claimed is:

1. A biosensor matrix comprising a substrate of semiconductor material and presenting a main plane surface and open cavities formed in a plane surface opposite from said main plane surface, and wherein deformable structures including at least one piezoresistive or piezoelectric sensing element are disposed between the bottoms of said cavities and said main plane surface.

2. A matrix according to claim 1, wherein at least one deformable structure is a membrane.

3. A matrix according to claim 1, wherein at least one deformable structure comprises at least one beam.

4. A matrix according to claim 1, wherein at least one deformable structure presents a plurality of said sensing elements in a bridge circuit.

5. A matrix according to claim 1, wherein the substrate is made of silicon.

6. A matrix according to claim 5, wherein the substrate presents a buried layer of $SiO_2$.

7. A matrix according to claim 1, wherein at least one deformable structure includes at least one piezoresistive sensing element.

8. A matrix according to claim 1, wherein at least one deformable structure presents at least one piezoelectric sensing element deposited on the substrate.

9. A matrix according to claim 1, wherein the main plane surface presents metallization enabling electrical connections to be made to said sensing elements.

10. A method of fabricating a matrix of biosensors according to claim 1, the method implementing:
  a) making said sensing elements in first localized locations of the main plane surface of the substrate; and
  b) making said cavities at second localized locations in a second surface of the substrate which is opposite from the main plane surface, in order to obtain deformable structures, each including at least one said sensing element.

11. A method according to claim 10, wherein said sensing elements are piezoresistive, wherein the substrate is made of silicon, and wherein step a) comprises:
  $a_1$) depositing a masking layer on a first surface of the substrate;
  $a_2$) making openings in first localized locations of the masking layer; and
  $a_3$) implanting ions in order to make said piezoresistive sensing elements;
  and wherein step b) comprises:
  $b_1$) depositing a masking layer on the second surface of the substrate, opposite from its first surface;
  $b_2$) making openings at second localized locations in the masking layer; and
  $b_3$) making said cavities by chemical etching.

12. A method according to claim 11, wherein the substrate includes a buried layer of silica surmounted by a single crystal surface layer, and wherein step $a_1$) comprises depositing said masking layer on the surface of the single crystal surface layer which constitutes said first surface of the substrate, and wherein in step $b_3$) etching is continued at least as far as the buried silica layer which forms a stop layer.

13. A method according to claim 11, wherein step $a_3$) implements:
  $a_{31}$) implanting boron or $BF_2$; and
  $a_{32}$) thermal annealing.

14. A method according to claim 13, wherein step $a_{31}$) is preceded by pre-amorphization of the surface of the substrate at said first localized locations of the masking layer.

15. A method according to claim 14, wherein said pre-amorphization is performed by implanting Ge.

16. A method according to claim 11, including making electrodes for making electrical contact with the piezoresistive sensing elements.

17. A method according to claim 10, wherein the sensing elements are piezoresistive and wherein step a) comprises: depositing a piezoelectric layer at said first localized locations followed by crystallization annealing.

18. A method according to claim 17, including providing electrodes for making electrical contact with the piezoelectric sensing elements.

19. A method of using a biosensor matrix according to claim 1, the method implementing:
  a) a preliminary step of using said sensing elements to control the bearing force exerted by a sample-depositor device against each of the biosensors and/or the length of time during which a bearing force is applied by said sample-depositor device; and
  b) a dynamic detection step during which variations in the mass of the samples deposited on each of the biosensors are measured.

* * * * *

UNITED STATES PATENT AND TRADEMARK OFFICE
CERTIFICATE OF CORRECTION

PATENT NO. : 6,930,365 B2
DATED : August 16, 2005
INVENTOR(S) : Bergaud et al.

It is certified that error appears in the above-identified patent and that said Letters Patent is hereby corrected as shown below:

<u>Title page,</u>
Item [75], Inventors, "Nicu Livus" should read -- Liviu Nicu --.

Signed and Sealed this

Twenty-seventh Day of December, 2005

JON W. DUDAS
*Director of the United States Patent and Trademark Office*